US00PP18107P2

(12) United States Plant Patent
Pieters

(10) Patent No.: US PP18,107 P2
(45) Date of Patent: Oct. 2, 2007

(54) ***CHRYSANTHEMUM* PLANT NAMED 'PPP TRI WH05'**

(50) Latin Name: *Chrysanthemum morifolium*
Varietal Denomination: PPP TRI WH05

(75) Inventor: Dirk Pieters, Oostnieuwkerke (BE)

(73) Assignee: Pieters Plant Production, Oostnieuwkerke (BE)

( * ) Notice: Subject to any disclaimer, the term of this patent is extended or adjusted under 35 U.S.C. 154(b) by 0 days.

(21) Appl. No.: 11/414,884

(22) Filed: Apr. 29, 2006

(51) Int. Cl.
*A01H 5/00* (2006.01)

(52) U.S. Cl. ..... Plt./288

(58) Field of Classification Search ..... Plt./288
See application file for complete search history.

*Primary Examiner*—Kent Bell
*Assistant Examiner*—June Hwu

(57) ABSTRACT

A new and distinct *Chrysanthemum* plant cultivar is disclosed, characterized by large decorative type inflorescences, consistent flowering response to short days, blooming consistently after 49 days of short day length, white ray florets with a creamy yellow center, free branching habit, and a consistent natural season flowering habit during the first week of September.

1 Drawing Sheet

Latin name of the genus and species: *Chrysanthemum morifolium.*
Variety denomination: 'PPP TRI WH05'.

BACKGROUND OF THE INVENTION

The new cultivar 'PPP TRI WH05' is a product of a cross between the female parent 'Rome' (U.S. Plant Pat. No. 13,032) and the male parent 'GEDI TWO PAD' (U.S. Plant Pat. No. 14,501). The new cultivar was discovered and selected by Dirk Pieters in September 2003 in Oostnieuwkerke, Belgium.

Asexual reproduction of the new cultivar 'PPP TRI WH05' by terminal cuttings and tissue culture was performed in Oostnieuwkerke, Belgium and Oxnard, Calif., and has shown that the unique features of this new cultivar are stable and reproduced true to type on successive generations.

SUMMARY OF THE INVENTION

The cultivar 'PPP TRI WH05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'PPP TRI WH05.' These characteristics in combination distinguish 'PPP TRI WH05' as a new and distinct *Chrysanthemum* cultivar:

1. Large decorative inflorescence with white ray florets and a creamy yellow center;
2. Consistent flowering response to short days, blooming consistently after 49 days of short day length;
3. Free branching habit; and
4. Consistent natural season flowering habit during the first week of September.

Plants of the new cultivar 'PPP TRI WH05' are similar to plants of the female parent variety, 'Rome' in most horticultural characteristics, however plants of the new cultivar 'PPP TRI WH05' are taller and wider than the female parent. Also, 'PPP TRI WH05' have a decorative inflorescence form compared to the anemone form of the female parent. Finally, 'PPP TRI WH05' has more inflorescences per lateral branch and a wider inflorescence diameter.

Plants of the new cultivar 'PPP TRI WH05' are similar to plants of the male parent 'GEDI TWO PAD' in most horticultural characteristics, however plants of the new cultivar 'PPP TRI WH05' are shorter in height but wider in plant spread than the male parent. Also, 'PPP TRI WH05' has more inflorescences per lateral branch and a wider inflorescence diameter. Finally, the new cultivar 'PPP TRI WH05' has white ray florets compared to the purple florets of the male parent.

In comparison to the commercially available variety 'GEDI THREE GEN' (U.S. Plant Pat. No. 17,202), 'PPP TRI WH05' is shorter and wider. Additionally, the new variety 'PPP TRI WH05' has a creamier white inflorescence than the comparable variety 'GEDI THREE GEN.' Further, the new variety 'PPP TRI WH05' has a smaller inflorescence diameter and smaller ray florets than the comparable variety. Finally, the disc florets of 'PPP TRI WH05' are a much brighter orange-yellow compared to the very pale yellow-white disc florets of 'GEDI THREE GEN.'

BRIEF DESCRIPTION OF THE PHOTOGRAPH

The accompanying photograph in FIG. 1 illustrates in full color a typical plant of 'PPP TRI WH05' grown in a 2 gallon container. One cutting was used in the pot, planted mid May and grown under outdoor field conditions. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used. The following observations and measurements describe 'PPP TRI WH05' plants grown in Oxnard, Ventura County, Calif., during the months of May through September 2005. The growing temperature ranged from 12° C. to 15° C. at night to 12° C. to 20° C. during the day. Measurements and numerical values represent averages of typical flowering types.

Botanical classification: *Chrysanthemum morifolium* cultivar 'PPP TRI WH05.'
Commercial classification: Garden-type *Chrysanthemum*.

PROPAGATION

Time to rooting: 7 to 14 days at approximately 21° C.
Root description: Fine, fibrous.

PLANT

Growth habit: Mounding herbaceous perennial.
Height: Approximately 23 cm.
Plant spread: Approximately 58 cm.
Growth rate: Moderate.
Branching characteristics: Free Branching.
Length of lateral branches: Approximately 19 cm.
Number of leaves per lateral branch: Approximately 30.
Age of plant described: Approximately 125 days.

FOLIAGE

Leaf:
- *Arrangement.*—Alternate single.
- *Average length.*—Approximately 3.5 cm.
- *Average width.*—Approximately 2.3 cm.
- *Shape of blade.*—Ovate.
- *Apex.*—Acuminate.
- *Base.*—Attenuate.
- *Attachment.*—Stalked.
- *Margin.*—Deeply lobed.
- *Texture of top surface.*—Lightly pubescent.
- *Texture of bottom surface.*—Lightly pubescent.
- *Leaf internode length.*—Approximately 2 cm.
- *Color.*—Young foliage upper side: Near Green 137A. Young foliage under side: Near Green 138B. Mature foliage upper side: Near Green 137A. Mature foliage under side: Near Green 138B.
- *Venation.*—Type: Palmately net. Venation color upper side: Near Green 138D. Venation color under side: Near Green 138D.

Petiole:
- *Average length.*—Approximately 1.7 cm.
- *Color.*—Near Green 138B.
- *Diameter.*—Approximately 0.1 cm.

BLOOM

Inflorescence:
- *Flowering habit.*—Induced by darkness period greater than 13.5 hours, approximately 49 days of appropriate day length required to induce and develop blooms.
- *Inflorescence form.*—Decorative.
- *Natural flowering season.*—Approximately first week in September.
- *Number of inflorescences per lateral branch.*—Approximately 24.
- *Inflorescence diameter.*—Approximately 5 cm.
- *Inflorescence depth.*—Approximately 2 cm.
- *Inflorescence longevity on plant.*—Approximately 28 to 32 days.
- *Persistence.*—Persistent.
- *General flower color.*—White with a yellow center.

Ray florets:
- *Appearance.*—Matte.
- *Texture.*—Smooth.
- *Average number of ray florets per inflorescence.*—165.
- *Shape.*—Oblanceolate.
- *Aspect.*—Flat.
- *Margin.*—Entire.
- *Apex.*—Obtuse.
- *Length.*—Approximately 2.2 cm.
- *Width.*—Approximately 0.5 cm.
- *Color.*—Upper surface at first opening: Near Yellow 4C. Upper surface at maturity: Near White 155B. Upper surface at fading: Near White 155B. Under surface at first opening: Near White 155B. Under surface at maturity: Near White 155B. Under surface at fading: Near White 155B.

Disc florets:
- *Appearance.*—Shiny.
- *Texture.*—Smooth.
- *Average number of florets per disc.*—Approximately 37.
- *Shape.*—Cylindric.
- *Apex.*—Obtuse.
- *Average length.*—Approximately 0.5 cm.
- *Average width.*—Approximately 0.1 cm.
- *Color.*—At first opening: Near Yellow 2A. At maturity: Near Yellow 13A. At fading: Near Yellow 13A.

Peduncle:
- *Length.*—At terminal end (shortest): Approximately 2.5 cm. At lateral end (longest): Approximately 3.9 cm.
- *Angle to stem.*—Acute.
- *Strength.*—Moderate.
- *Color.*—Near Green 138C.
- *Habit.*—Upright.
- *Diameter.*—Approximately 0.1 cm.
- *Surface texture.*—Lightly pubescent.

Inflorescence bud:
- *Length.*—Approximately 0.5 cm.
- *Diameter.*—Approximately 0.5 cm.
- *Form.*—Globular.
- *Color.*—Near Green 138C.

Involucral bracts (phyllaries):
- *Appearance.*—Matte.
- *Texture.*—Lightly pubescent.
- *Number.*—Approximately 25.
- *Shape.*—Ovate.
- *Margin.*—Entire.
- *Apex.*—Acute.
- *Length.*—Approximately 0.6 cm.
- *Width.*—Approximately 0.3 cm.
- *Color.*—Upper side: Near Green 137C. Under side: Near Green 137C.

REPRODUCTIVE ORGANS

Ray florets:
- *Number of pistils per floret.*—1.
- *Stigma shape.*—2 branched.
- *Stigma color.*—Near Yellow 13A.
- *Style color.*—Near White 155B.
- *Style length.*—Approximately 0.3 cm.
- *Stamens.*—Absent.

Disc florets:

*Number of pistils per floret.*—1.
*Stigma shape.*—Cylindric.
*Stigma color.*—Near Yellow 13A.
*Style length.*—Approximately 0.3 cm.
*Style color.*—Near Yellow-Green 154D.
*Number of stamens per floret.*—Approximately 5.
*Anther shape.*—Tubular.
*Anther color.*—Near Yellow 13A.
*Pollen color.*—Near Yellow 13A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximate range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'PPP TRI WH05' as herein illustrated and described.

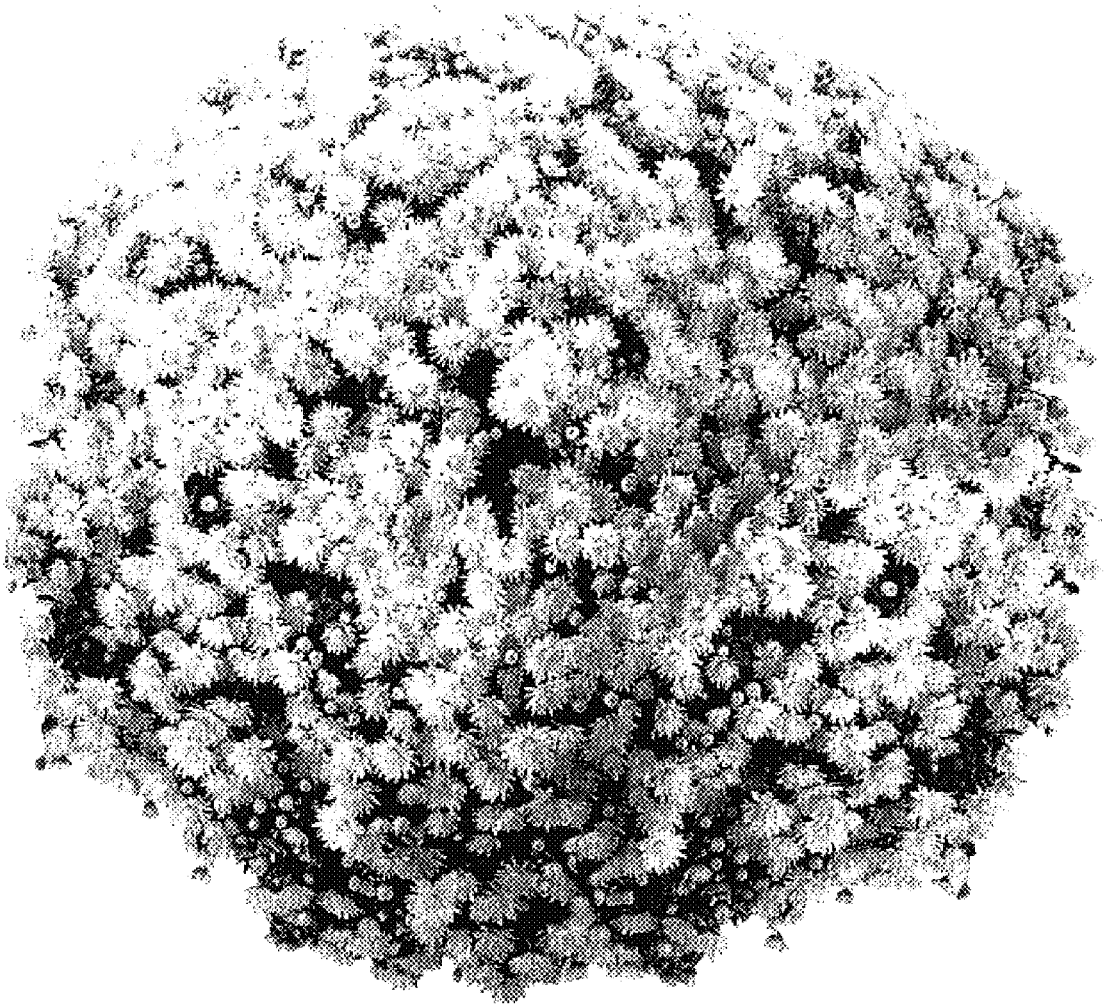

* * * * *